United States Patent [19]

Boebel

[11] Patent Number: 4,614,182
[45] Date of Patent: Sep. 30, 1986

[54] APPLICATOR FOR UTERINE PESSARIES

[75] Inventor: Manfred Boebel, Oetisheim, Fed. Rep. of Germany

[73] Assignee: Richard Wolf GmbH, Fed. Rep. of Germany

[21] Appl. No.: 632,288

[22] Filed: Jul. 19, 1984

[30] Foreign Application Priority Data

Mar. 30, 1984 [DE] Fed. Rep. of Germany ....... 3411768

[51] Int. Cl.$^4$ .......................... A61F 5/46; A61F 13/20
[52] U.S. Cl. ...................................... 128/130; 604/11; 604/12; 604/13; 604/14; 604/15; 604/16; 604/17; 604/18
[58] Field of Search ...................... 128/130; 604/11–18

[56] References Cited

U.S. PATENT DOCUMENTS 3,918,444 11/1975 Hoff et al. ............................ 128/130
3,965,891 6/1976 Lerner ................................. 128/130

Primary Examiner—Herbert S. Cockeram
Attorney, Agent, or Firm—Hill, Van Santen, Steadman & Simpson

[57] ABSTRACT

The applicator for inserting a pessary into the uterus, which pessary comprises a chain combined with a distal coil screwable into the base of the uterus. The applicator has an inner shaft, which received the chain in its leading end, installed in an outer shaft and with its leading end securing the nearer of the coil in a formlocked or forcelocked manner, as well as a handle at the opposite end of the shaft whose rotation and axial displacement allow screwing the coil out of the outer shaft and into the base of the uterus to the extend of its longitudinal dimension. The outer and inner shafts are withdrawable from the uterus with respect to the screwed-in coil and chain which are to be released, after completion of the application.

7 Claims, 4 Drawing Figures

APPLICATOR FOR UTERINE PESSARIES

BACKGROUND OF THE INVENTION

1. Field of the Invention

This invention relates to an applicator for inserting a pessary into the uterus, which pessary comprises a chain combined with a coil at the distal extremity, which coil may be screwed into the base of the uterus.

To prevent a woman from becoming pregnant, it is known that intrauterine pessaries or various spatial forms may be inserted into the uterus. These pessaries are equipped in part with a retrieval thread extending into the vagina. Threads of this nature may cause infections, and the position of the pessary may be altered by the movements of the wearer, and movements of the muscles of the uterus may cause an accidental ejection of the pessary from the uterus or even a perforation of the uterus.

2. Description of the Prior Art

It has recently been proposed that a chain be utilised as a pessary, which is equipped at the distal extremity with a coil which may be immobilised by being screwed into the base of the uterus, thereby securing the pessary reliably in the uterus and allowing trouble-free movement by the wearer. The insertion of chain pessaries of this nature still raises considerable problems however, since applicators which may be operated in an uncomplicated and reliable manner are still not available at present.

SUMMARY OF THE INVENTION

The object of the invention consists in establishing the possibility of utilising a comparatively uncomplicated and reliably manipulatable applicator with or without an optical system for the insertion of chain pessaries combined with a coil.

In accordance with the invention, this problem is resolved in that the said applicator comprises:

an inner shaft having a leading end to receive the chain and to hold the end of the coil attached to the chain in a formlocked or forcelocked manner;

an outer shaft to enclose said inner shaft therein and a handle at the end of the outer shaft remote from said leading end for screwing said leading end of the inner shaft out of said outer shaft under rotation and axial displacement together with said coil, in the longitudinal direction of the coil to screw the coil into the base of the uterus, the outer shaft being rearwardly displaceable on the inner shaft to release the chain.

The insertion of the pessary into the uterus with screwing of the coil into the base of the uterus may be performed in a very uncomplicated manner by means of an applicator of this kind. The applicator advantageously is utilised in combination with an endoscope optical system comprising an oblique eyepiece tube with a shaft which is equipped with an instrument passage intended for traversal by the applicator, so that the insertion of the pessary and above all the screwing of the coil into the base of the uterus may be performed under observation. The applicator may also be utilised without application of an endoscope optical system.

BRIEF DESCRIPTION OF THE DRAWINGS

The invention, together with other advantageous features, is described in the following with reference to the drawings in which an example of embodiment is illustrated. In the drawings.

DESCRIPTION OF THE INVENTION

Figure 1:
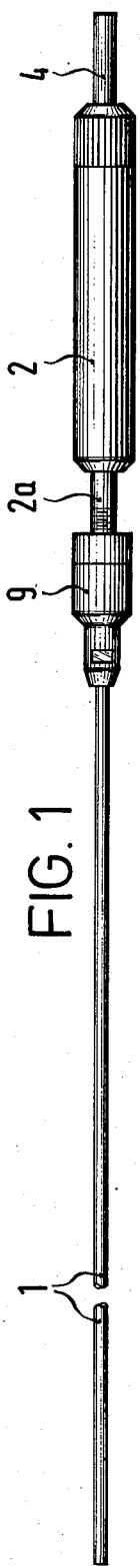
FIG. 1 is a side view of the applicator with an outer shaft illustrated with a portion cut away.
Figure 3:
FIG. 3 is an enlarged side view of the receiving element for the pessary and for the attached coil extremity.
Figure 2:
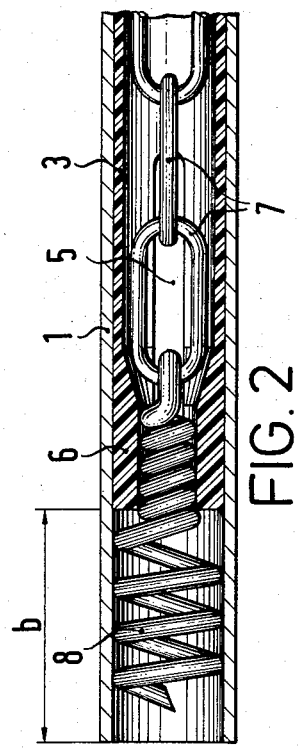
FIG. 2 is an enlarged axial cross-section of the applicator's leading end with the chain pessary inserted.
Figure 4:
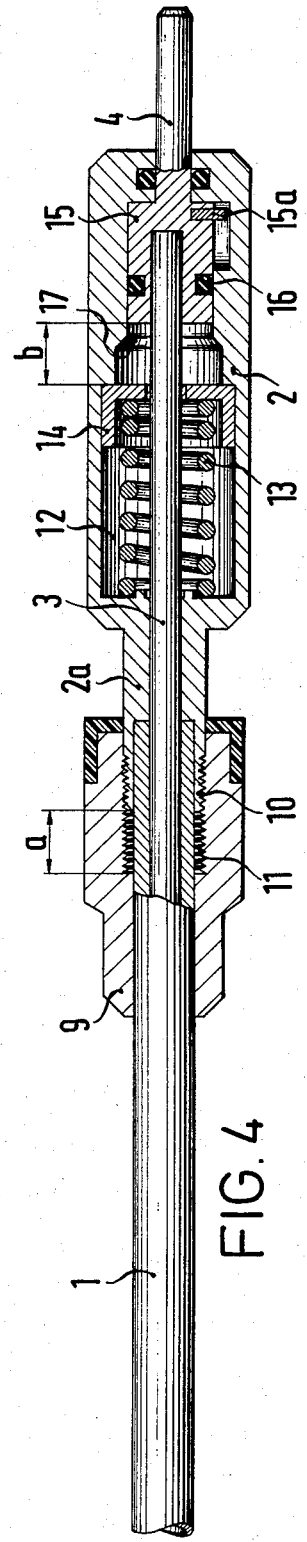
FIG. 4 is an enlarged axial cross-sectional view with portions in elevation of a rear end of the applicator of the present invention.

The applicator according to the invention comprises an outer tubular or hollow shaft 1 which is firmly joined at one end to a handle 2, and an inner tubular or hollow shaft 3, which is secured at one end directly to a thrust plunger 4 which is housed in the handle 2. The shaft 3 is equipped at its other end with two longitudinal slots 5 (FIG. 3) and has internal clamping jaws 6, e.g. of elastic material, at its leading end. The clamping jaws 6 are closed by the outer shaft 1 being pushed over the inner shaft, or by drawing the inner shaft into the outer shaft, by means of the resiliently yielding elements 3a, which immobilise the near end of a coil 8 which is connected to the chain 7 acting as a pessary which had been inserted into the inner shaft 3 beforehand. The leading end of the inner shaft may comprise an elastic tube which secures the near extremity of the coil 8 as soon as the outer shaft 1 is pushed over the inner shaft 3.

The outer shaft 1 passes slideably through a coupling member 9 which is coupled to a complementary coupling member of an instrument passage of a known endoscope optical system comprising an oblique eyepiece tube, which is not shown. The outer shaft is firmly joined to a cylindrical part 2a of the handle 2. The part 2a may be screwed by turning the handle 2 with an external screw-thread 10 into an internal screw-thread 11 of the coupling member 9, by a distance a, and the screw threads advantageously have the same pitch as those of the coil 8.

The handle 2 has a hollow cylindrical space 12 and a hollow plunger 14 displaceable therein, between which a compression spring 13 bears against the end face of the cylindrical space 12 on the one hand and an inner end surface of the hollow plunger 14 on the other hand. A piston 15 of the thrust plunger 4 is installed in an untwistable but axially displaceable manner in the rear portion of the handle 2 by means of a pin 15a. The end of the inner shaft 3 which traverses the handle 2 and the outer shaft 1 with little play in a freely slidable manner, is firmly joined to this piston 15. The piston 15 is provided around its periphery with an elastically deformable ring 16, e.g. a rubber ring, which releasably secures the piston in the idle rest position, as well as in a first advanced position, against accidental displacement.

The applicator, which is described in the foregoing and has the pessary inserted in it, is initially introduced into the sealed instrument passage of the endoscope optical system which is inserted into the uterus and the application is coupled thereto with the leading end of the outer shaft 1 being placed in the field of view of the optical system.

The applicator is then displaced together with the optical system under simultaneous observation within the uterus until the leading end of the outer shaft 1 and of the optical system are situated just in front of the base of the uterus. The coil 8 is then forwardly displaced by the distance b together with the inner shaft 3 by a distally directed pressure on the thrust plunger 4. The coil thus projects out of the outer shaft 1, so that this coil may be observed and offered up to the base. Upon actuating the thrust plunger 4, the piston 15 is displaced in the handle 2 by the distance b until the piston 15 is placed in contact with the hollow plunger 14 receiving the compression spring 13. At the same time, the ring 16 reaches the annular shoulder 17 in the area of the diametrical step, at which it sets the piston 15 and thus the coil 8 elastically with radially outwardly directed stress relief in the advanced position in front of the outer shaft.

As soon as this position is reached, the handle 2 is screwed in by the distance a into the coupling member 9 by being turned with the inner shaft 3 co-rotating with the secured coil 8, so that the coil 8 may thereby be screwed into the base of the uterus.

Finally, the outer shaft 1 and the endoscope are withdrawn from the uterus with the handle 2, the outer shaft 1 and the optical system then being withdrawn against the spring 13. The parts 3a of the seat may thereby spread resiliently outwards radially, so that the near end of the coil 8 secured in the uterus and the chain 5 are released and remain within the uterus, whereas the applicator may be pulled out with the endoscope optical system. In conclusion, it may be stated that the applicator may also be utilised without an optical system. It is then appropriate for the coupling member 9 also to be constructed as a handle.

I claim:

1. An applicator for inserting a pessary into the uterus, which pessary comprises a chain attached at one end thereof to one end of a coil for screwing the pessary into the base of the uterus, the applicator comprising:

an inner shaft having a hollow leading end to receive the chain and to hold the end of the coil which is attached to the chain in a formlocked or forcelocked manner;

an outer tubular shaft receiving said inner shaft therein for axial displacement; and a handle at the end of the outer shaft remote from said leading end for rotating the inner shaft to screw said leading end of the inner shaft out of said outer shaft with said coil in the longitudinal direction of the coil to screw the coil into the base of the uterus, said handle enables said outer shaft to be rearwardly displaceable on the inner shaft to release the chain.

2. An applicator according to claim 1, which includes a coupling member being axially displaceably received on the outer shaft and being threadedly connected to a cylindrical end of the handle which is connected to said outer shaft, said coupling member being connectable to a coupling member of an instrument passage of an optical system of an endoscope.

3. An applicator according to claim 1, wherein the inner shaft is secured in a first plunger in the handle, said first plunger may be displaced without being twisted within the handle until said first plunger impinges against an end of a hollow second plunger to form an advanced position with the coil projecting distally out of the outer shaft by a predetermined distance.

4. An applicator according to claim 1, wherein the handle has a cylindrical cavity wherein a spring operates between the end face of the cavity nearest the pessary and the hollow second plunger, said hollow plunger being longitudinally displaceable therein, the spring and the hollow plunger being freely traversed by the end of the inner shaft secured to the first plunger, the first plunger having a portion projecting out of the handle and the first and second plungers having a predetermined mutual spacing in the idle rest position.

5. An applicator according to claim 4, wherein the first plunger may be secured in said advanced position in contact with the hollow second plunger under initial spring loading by an elastic ring which expands radially as pressure on it is released and bears against an annular shoulder in the handle.

6. An applicator according to claim 1, wherein the inner shaft has at its leading end two or more longitudinal slots defining between them receiving elements subject to initial spring loading in a radially outward direction, said receiving elements being equipped at their outer extremity with an inner wall reinforcement for securing the proximal extremity of the coil in formlocked or forcelocked manner when the outer shaft engages over the leading end of the inner shaft.

7. An applicator according to claim 1, wherein the inner shaft has at its leading end a receiving member comprising a tubular portion laid resiliently around the proximal extremity of the coil to secure the coil in a forcelocked manner when the outer shaft engages over the same.

* * * * *